United States Patent
Gott et al.

[11] Patent Number: 6,054,613
[45] Date of Patent: Apr. 25, 2000

[54] PROCESS FOR THE PRODUCTION OF SULPHONAMIDES

[75] Inventors: Brian David Gott; James Peter Muxworthy; Stephen Martin Brown, all of Huddersfield, United Kingdom

[73] Assignee: Zeneca Limited, United Kingdom

[21] Appl. No.: 09/308,742

[22] PCT Filed: Nov. 27, 1997

[86] PCT No.: PCT/GB97/03272

§ 371 Date: May 24, 1999

§ 102(e) Date: May 24, 1999

[87] PCT Pub. No.: WO98/25890

PCT Pub. Date: Jun. 18, 1998

[30] Foreign Application Priority Data

Dec. 11, 1996 [GB] United Kingdom ................... 9625781

[51] Int. Cl.$^7$ ..................... C07C 303/44; C07C 303/38
[52] U.S. Cl. ................................. 564/98; 564/99
[58] Field of Search ........................ 564/98, 99

[56] References Cited

U.S. PATENT DOCUMENTS 5,455,377  10/1995  Ronchi et al. ........................ 569/98

FOREIGN PATENT DOCUMENTS 0 373 557  9/1989  European Pat. Off. .
0 439 687  8/1991  European Pat. Off. .

OTHER PUBLICATIONS

Chem Abst., vol. 119, No. 9, Abstract No. 95095x, 1993.

*Primary Examiner*—Peter O'Sullivan
*Attorney, Agent, or Firm*—Marian T. Thomson

[57] ABSTRACT

A process for the preparation of a sulfonamide of formula:

$$RSO_2NR^1R^2$$

wherein R represents $C_1$–$C_{10}$ alkyl; and
$R^1$ and $R^2$ independently represent hydrogen, $C_1$–$C_{10}$ alkyl or $C_6$–$C_{10}$ aryl; which comprises reacting the corresponding alkane- or arenesulfonyl halide of formula:

$$RSO_2Hal$$

wherein Hal represents halogen; with the corresponding compound of formula:

$$NHR^1R^2$$

in an aqueous solvent and extracting the sulfonamide from the resulting mixture into a polar organic solvent.

8 Claims, No Drawings

PROCESS FOR THE PRODUCTION OF SULPHONAMIDES

The present invention relates to a process for the preparation of alkane-sulphonamides, in particular, to a process for obtaining a solution of an alkane-sulphonamide in a polar organic solvent.

Alkane- and arenesulphonamides are well known and are useful as intermediates in various aspects of chemistry, for example in the synthesis of herbicidally active compounds. Conventionally sulphonamides are produced by the reaction of a sulphonyl halide with the corresponding primary or secondary amine or ammonia, for example:

$$RSO_2Cl + 2NH_3 \rightarrow RSO_2NH_2 + NH_4Cl$$

A variety of documents describe syntheses of this type in organic solvents, for example U.S. Pat. No. 5,455,377 discloses the use of an aliphatic nitrile, e.g. acetonitrile, as solvent, and EP 519235 discloses the use of dioxolane as solvent. The use of organic solvents has the disadvantage that it requires a recycle system and the containment of what are usually volatile and expensive solvents. In addition such processes result in the production of a solvent wet ammonium halide or amine hydrohalide which can cause disposal problems.

EP 439687 discloses a process for the production of alkane- and arenesulphonamides under boiling conditions in the absence of an additional solvent. This process has the drawback that it requires the use of anhydrous ammonia or amine. The ammonium halide or amine hydrohalide by-product which is produced in this reaction may be treated with an alkali metal hydroxide, e.g. sodium or potassium hydroxide, to give the corresponding alkali halide salt and free ammonia or alkylamine which can be recovered. The sulphonamide/salt mixture may be used directly for its intended purpose or the sulphonamide can be recovered from the salt by solvent extraction followed by filtration. As a comparative example EP 439687 discloses a process for the production of methanesulphonamide using aqueous ammonium hydroxide. However, in this particular example once the reaction is complete the water is evaporated under reduced pressure but no attempt is made to separate the resulting methanesulphonamide and ammonium chloride.

EP 333557 discloses a process for making arylsulphonamides from arylsulphonyl halides which results in a two-phase mixture.

The present invention provides a process for the preparation of a sulphonamide of formula:

$$RSO_2NR^1R^2$$

wherein R represents $C_1$–$C_{10}$ alkyl; and
$R^1$ and $R^2$ independently represent hydrogen, $C_1$–$C_{10}$ alkyl or $C_6$–$C_{10}$ aryl; which comprises reacting the corresponding alkane- or arenesulphonyl halide of formula:

$$RSO_2Hal$$

wherein Hal represents halogen; with the corresponding compound of formula:

$$NHR^1R^2$$

in an aqueous solvent and extracting the sulphonamide from the resulting mixture into a polar organic solvent.

The process of the invention may be performed as a batch, semi-continuous or continuous process.

Alkanesulphonamides produced according to the invention may contain straight chain, branched or cyclic $C_1$–$C_{10}$ alkyl groups. The process is particularly useful for the preparation of short chain alkanesulphonamides, e.g. $C_1$–$C_4$ alkanesulphonamides, especially methane- and ethane-sulphonamide.

The sulphonyl halide of formula $RSO_2Hal$ used as starting material is preferably a sulphonyl chloride.

When $R^1$ and $R^2$ represent $C_1$–$C_{10}$ alkyl or $C_6$–$C_{10}$ aryl particular groups they may represent include phenyl, naphthyl and straight chain, branched or cyclic $C_1$–$C_{10}$ alkyl groups. However, $R^1$ and $R^2$ preferably represent hydrogen, i.e. the compound of formula $NHR^1R^2$ is ammonia.

The starting materials required for the process are either commercially available or may be prepared by methods known to the skilled person.

In the process of the invention the sulphonyl halide is preferably added to an aqueous solution of the compound of formula $NHR^1R^2$. The solution of the compound $NHR^1R^2$ used in the reaction is preferably a 10–35% solution, more preferably a saturated solution. The mol ratio of compound $NHR^1R^2$ to sulphonyl halide used in the reaction is preferably from about 2.5 to about 5.0, more preferably from 3.0 to 4.0. The addition of the sulphonyl halide to the reaction mixture is preferably conducted at a temperature of from ambient to about 80° C., preferably at a temperature of from 25 to 50° C.

In the process of the invention a base is preferably added to the reaction mixture to allow displacement and recovery of the excess compound of formula $NHR^1R^2$. The base is preferably an alkali or alkaline earth metal hydroxide or carbonate or an alkaline earth metal oxide, particular bases that may be mentioned include sodium hydroxide, calcium oxide and calcium hydroxide. Calcium oxide and calcium hydroxide are particularly preferred as they give a calcium chloride brine which has the advantages of a high saturation value giving increased process productivity and increased solvent extraction efficiency, and a high density giving improved separation of the solvent and aqueous phases. The mol ratio of base used is preferably 1 to 1.05 for alkali metal hydroxides and 0.5 to 0.53 for alkali metal carbonates and alkaline earth metal hydroxides and oxides. The addition of the base to the reaction mixture is preferably conducted at a temperature of from about 50° C. to about 90° C., preferably at a temperature of from 60 to 70° C.

According to a further aspect the invention provides a process for the preparation of a sulphonamide of formula:

$$RSO_2NR^1R^2$$

wherein R represents $C_1$–$C_{10}$ alkyl or $C_6$–$C_{10}$ aryl; and $R^1$ and $R^2$ independently represent hydrogen, $C_1$–$C_{10}$ alkyl or $C_6$–$C_{10}$ aryl; which comprises reacting the corresponding alkane- or arenesulphonyl halide of formula:

$$RSO_2Hal$$

wherein Hal represents halogen; with the corresponding compound of formula:

$$NHR^1R^2$$

in an aqueous solvent followed by displacement of excess compound of formula $NHR^1R^2$ by the addition of a base selected from calcium hydroxide and calcium oxide.

A wide variety of organic solvents may be used to extract the sulphonamide from the aqueous reaction mixture but it has been found that some polar solvents, for example nitriles such as acetonitrile, ketones such as methyl ethyl ketone or acetone, ethers such as tetrahydrofuran, and esters such as ethyl acetate are particularly suitable. Particularly preferred solvents are acetonitrile, tetrahydrofuran and methyl ethyl ketone.

The extraction may be performed at a temperature ranging from ambient to about 70° C. depending on the boiling point of the solvent used. The extraction efficiency of the process may be improved by performing the extraction at elevated temperature, for example at a temperature of from 40 to 60° C., preferably at about 50° C.

The extraction process may be performed using any conventional extraction procedure, for example multiple batch extraction or counter-current continuous liquid-liquid extraction.

The resulting solvent solution of the alkane- or arenesulphonamide may be partially distilled to concentrate the solution and remove water or it can be evaporated to give a melt of the sulphonamide.

The residual aqueous solution obtained after completion of the extraction process will be saturated with the extraction solvent, depending on the solvent used, this may be present at a concentration of from about 1–10% w/w. The aqueous solution may be steam stripped to recover the extraction solvent for recycling.

The process of the invention has the advantage that excess ammonia or amine can be removed after completion of the reaction and recycled within the reaction system. In addition, the organic solvent into which the product is extracted may be partially distilled off to give a concentrated solution of the alkane- or arenesulphonamide and the distillate may be recycled and reused to extract further product. The process does not generate solid inorganics contaminated with solvent, neither does it create waste ammonium halide or amine hydrohalide, also the solvent does not have to be kept dry.

The reaction will now be further described with reference to the following examples.

EXAMPLE 1
Preparation of methane sulphonamide with calcium oxide as base and extraction into acetonitrile Aqueous ammonia (170 g, 35%, 3.5 mol) was charged to a clean dry split reaction vessel and methane sulphonyl chloride (100 g, 99%, 0.865 mol) added dropwise with stirring. During the addition, the temperature was allowed to rise to 65 to 70° C. This temperature was maintained during the addition of calcium oxide (25.7 g, 98%, 0.45 mol). The resulting white suspension was gradually heated to 90° C. and held at that temperature for 6 hours while purging with nitrogen to remove residual ammonia. Once no further ammonia was being removed from the reaction mixture, the temperature of the mixture was adjusted to 50° C. Acetonitrile (206 ml—about equal volume to the aqueous phase) was charged to the flask and agitated for 15 min. The mixture was allowed to settle for about 15 min before the aqueous and organic phases were separated. The extraction was repeated twice using acetonitrile volumes of 190 and 154 ml respectively at a temperature of 50° C. throughout. The extracts were combined to yield an acetonitrile solution containing 12.6% methane sulphonamide (87.5% yield) and 8.6% water.

EXAMPLE 2
Preparation of methane sulphonamide with sodium hydroxide as base and extraction into acetonitrile Aqueous ammonia (170 g, 35%, 3.5 mol) was charged to a clean dry split reaction vessel with a turbine agitator at 220 rpm. Methane sulphonyl chloride (100 g, 99%, 0.865 mol) added dropwise with stirring. During the addition, the temperature was allowed to rise to 65 to 70° C. and this temperature maintained during the addition of sodium hydroxide liquor (70 g, 50%, 0.875 mol). After addition of the sodium hydroxide liquor the temperature was raised to 90° C. and held at that temperature while purging with nitrogen to remove residual ammonia which was collected in a hydrochloric acid trap. Once no further ammonia was being removed from the reaction mixture, the temperature of the mixture was adjusted to 50° C. and the solution extracted with an equal volume of acetonitrile (241 ml). The extraction was repeated twice using acetonitrile volumes of 232 and 169 ml respectively at a temperature of 50° C. throughout. The extract weights were as follows:

First extract: 16.6% w/w=34.7 g methane sulphonamide.

Second extract: 9.5% w/w=22.7 g methane sulphonamide.

Third extract: 9.1% w/w=5.7 g methane sulphonamide.

The extracts were combined and the acetonitrile removed by distillation at 75° C. and 200–300 mm Hg to give crystalline methane sulphonamide at 96.6% strength.

We claim:

1. A process for the preparation of a sulphonamide of formula:

$$RSO_2NR^1R^2$$

wherein R represents $C_1$–$C_{10}$ alkyl; and $R^1$ and $R^2$ independently represent hydrogen, $C_1$–$C_{10}$ alkyl or $C_6$–$C_{10}$ aryl; which comprises reacting the corresponding alkane- or arenesulphonyl halide of formula:

$$RSO_2Hal$$

wherein Hal represents halogen; with the corresponding compound of formula:

$$NHR^1R^2$$

in an aqueous solvent and extracting the sulphonamide from the resulting mixture into a polar organic solvent.

2. A process according to claim 1 wherein $R^1$ and $R^2$ represent hydrogen.

3. A process according to claim 1, for the preparation of methane sulphonamide.

4. A process according to claim 1, wherein the compound of formula $RSO_2Hal$ is a sulphonyl chloride.

5. A process according to claim 1, wherein the solvent used to extract the product from the aqueous reaction mixture is a nitrile, a ketone, an ether or an ester.

6. A process according to claim 5, wherein the solvent is acetonitrile, methyl ethyl ketone or tetrahydrofuran.

7. A process according to claim 1, wherein the excess compound of formula $NHR^1R^2$ is removed after completion of the reaction by displacement with base.

8. A process according to claim 7, wherein the base is calcium oxide or calcium hydroxide.

* * * * *